United States Patent
Kawano et al.

(10) Patent No.: US 10,752,575 B2
(45) Date of Patent: Aug. 25, 2020

(54) 4-ALKOXY-3-(TRIFLUOROMETHYL)BENZYL ALCOHOL PRODUCTION METHOD

(71) Applicant: MITSUBISHI TANABE PHARMA CORPORATION, Osaka-shi, Osaka (JP)

(72) Inventors: Makoto Kawano, Osaka (JP); Takashi Naka, Osaka (JP); Mitsuharu Nakamura, Osaka (JP); Hisao Takayanagi, Yokohama (JP)

(73) Assignee: MITSUBISHI TANABE PHARMA CORPORATION, Osaka-Shi (JP)

( * ) Notice: Subject to any disclaimer, the term of this patent is extended or adjusted under 35 U.S.C. 154(b) by 0 days.

(21) Appl. No.: 16/321,299

(22) PCT Filed: Jul. 28, 2017

(86) PCT No.: PCT/JP2017/027388
§ 371 (c)(1),
(2) Date: Jan. 28, 2019

(87) PCT Pub. No.: WO2018/021517
PCT Pub. Date: Feb. 1, 2018

(65) Prior Publication Data
US 2019/0161432 A1    May 30, 2019

(30) Foreign Application Priority Data

Jul. 29, 2016  (JP) .................. 2016-149905

(51) Int. Cl.
| C07C 41/26 | (2006.01) |
| C07C 213/02 | (2006.01) |
| C07C 43/23 | (2006.01) |
| C07C 217/64 | (2006.01) |

(52) U.S. Cl.
CPC .......... *C07C 213/02* (2013.01); *C07C 41/26* (2013.01); *C07C 43/23* (2013.01); *C07C 217/64* (2013.01)

(58) Field of Classification Search
None
See application file for complete search history.

(56) References Cited

U.S. PATENT DOCUMENTS

| 2009/0137530 A1 | 5/2009 | Kiuchi et al. |
| 2010/0179216 A1 | 7/2010 | Kiuchi et al. |
| 2014/0296183 A1 | 10/2014 | Kiuchi et al. |

FOREIGN PATENT DOCUMENTS

| EP | 2 354 134 A1 | 8/2011 |
| WO | WO 2007/069712 A1 | 6/2007 |
| WO | WO 2009/119858 A1 | 10/2009 |

OTHER PUBLICATIONS

Shu et al., "A Survey of electron-deficient pentacenes as acceptors in polymer bulk hereojunction solar cells," Chem. Sci., vol. 2, 2011, pp. 363-368, with supplemental material pp. S-1-S-19 (25 pages total).
Extended European Search Report for European Application No. 17834519.5, dated Mar. 6, 2020.

*Primary Examiner* — Sudhakar Katakam
*Assistant Examiner* — Jennifer C Sawyer
(74) *Attorney, Agent, or Firm* — Birch, Stewart, Kolasch & Birch, LLP

(57) ABSTRACT

The present invention relates to a production method of 4-alkoxy-3-trifluoromethylbenzyl alcohol at a high conversion ratio, which can strictly suppress production of a byproduct by using DIBAL as a reducing agent.

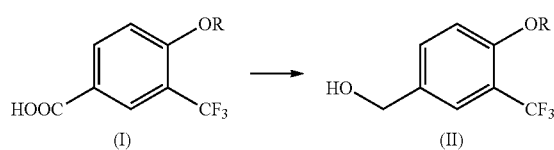

17 Claims, No Drawings

4-ALKOXY-3-(TRIFLUOROMETHYL)BENZYL ALCOHOL PRODUCTION METHOD

TECHNICAL FIELD

The present invention relates to a method of reducing a benzoic acid derivative to a benzyl alcohol derivative, and particularly relates to a production method of 4-alkoxy-3-trifluoromethylbenzyl alcohol useful as a production intermediate for pharmaceutical products.

BACKGROUND ART

Cited document 1 discloses a production method of 2-amino-2-[2-(4-heptyloxy-3-trifluoromethylphenyl)ethyl]propane-1,3-diol hydrochloride useful as a medicament superior in an immunosuppressive action, a rejection suppressive action and the like.

The production method includes a step of reducing 4-heptyloxy-3-trifluoromethylbenzoic acid (Ia) to 4-heptyloxy-3-trifluoromethylbenzyl alcohol (IIa). However, this step has a problem of low conversion ratio or a problem of production of byproduct (IIa') resulted by reduction of a trifluoromethyl group along with compound (IIa).

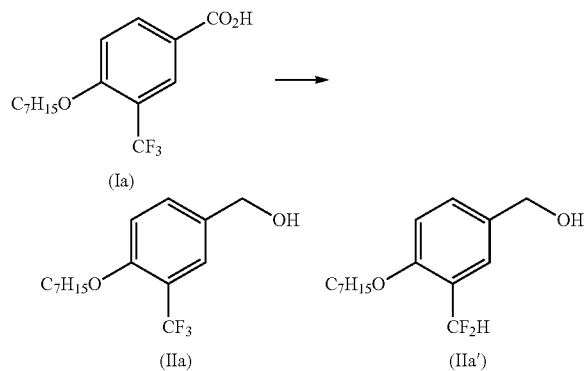

Particularly, since a series of analogues derived from byproduct (IIa') are difficult to remove in the subsequent steps, the production of a drug substance for pharmaceutical products requested to have high quality requires strict suppression of the production thereof.

DOCUMENT LIST

Patent Document patent document 1: WO 2007/069712

SUMMARY OF THE INVENTION

Problems to be Solved by the Invention

An object of the present invention is to provide a production method of 4-alkoxy-3-trifluoromethylbenzyl alcohol, which shows high conversion ratio, and can strictly suppress production of a byproduct.

Means of Solving the Problems

The present inventors have conducted intensive studies in an attempt to solve the above-mentioned problem and found that compound (II) can be produced at a high conversion ratio and without producing a byproduct resulted by reduction of a trifluoromethyl group by using, as a reducing agent, DIBAL (diisobutylaluminum hydride) comparatively easily usable at a commercial production scale in a step for reducing 4-alkoxy-3-trifluoromethylbenzoic acid (hereinafter to be also referred to as compound (I)) to 4-alkoxy-3-trifluoromethylbenzyl alcohol (hereinafter to be also referred to as compound (II)), which resulted in the completion of the present invention.

Therefore, the present invention provides the following.

[1] A production method of a compound represented by the following formula (II) (i.e., compound (II)), the method comprising reducing a compound represented by the following formula (I) (i.e., compound (I)) by using diisobutylaluminum hydride:

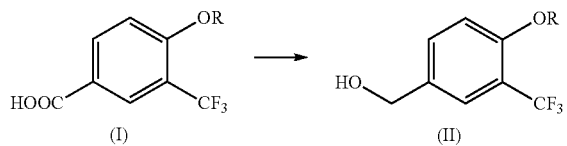

wherein R is alkyl having 1 to 10 carbon atoms.

[2] A production method of a compound represented by the following formula (IV) (hereinafter to be also referred to as compound (IV)) or a pharmaceutically acceptable acid addition salt thereof, the method comprising dialkyl-phosphonate-esterifying a hydroxyl group of a compound represented by the following formula (II) (i.e., compound (II)) obtained by the method described in the above-mentioned [1], reacting the resultant compound with a compound represented by the following formula (III) (hereinafter to be also referred to as compound (III)), and hydrolyzing and further reducing the obtained compound:

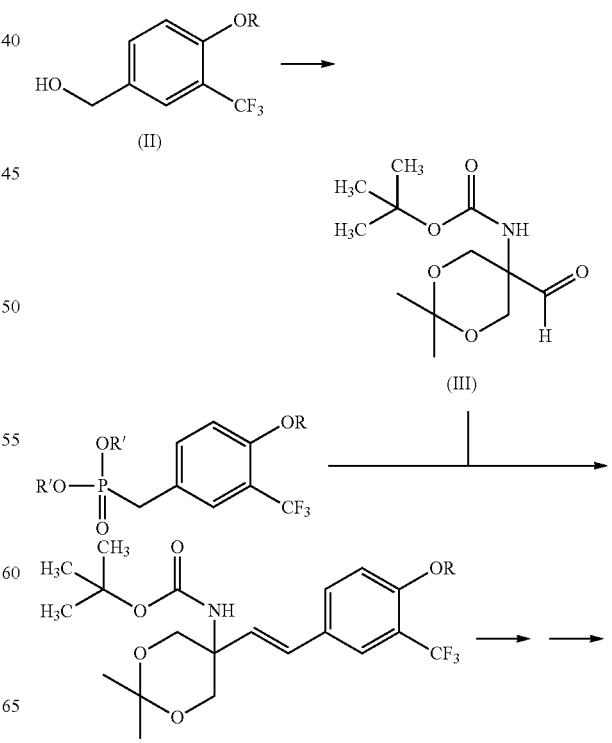

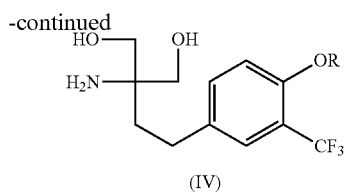

wherein R is alkyl having 1 to 10 carbon atoms, and R' is alkyl having 1 to 3 carbon atoms.

[3] The production method of the above-mentioned [1] or [2], wherein R is a heptyl group.

[4] The production method of the above-mentioned [2], wherein R is a heptyl group, and the compound represented by the formula (IV) (i.e., compound (IV)) or a pharmaceutically acceptable acid addition salt thereof is 2-amino-2-[2-(4-heptyloxy-3-trifluoromethylphenyl)ethyl]propane-1,3-diol.

[5] The production method of the above-mentioned [2], wherein R is a heptyl group, and the compound represented by the formula (IV) (i.e., compound (IV)) or a pharmaceutically acceptable acid addition salt thereof is 2-amino-2-[2-(4-heptyloxy-3-trifluoromethylphenyl)ethyl]propane-1,3-diol hydrochloride.

Effect of the Invention

According to the present invention, 4-alkoxy-3-trifluoromethylbenzyl alcohol can be produced at a high conversion ratio while strictly suppressing the production of a byproduct.

DESCRIPTION OF EMBODIMENTS

The present invention provides a production method of compound (II) comprising reducing compound (I) by using diisobutylaluminum hydride. This production method is shown by the following Step 1.

(Step 1)

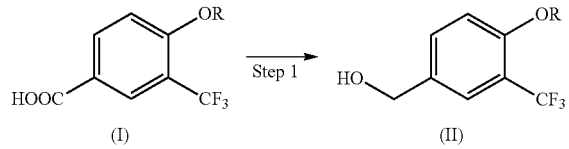

wherein R is alkyl having 1 to 10 carbon atoms.

Examples of the "alkyl having 1 to 10 carbon atoms" for R include methyl, ethyl, propyl, isopropyl, butyl, isobutyl, sec-butyl, tert-butyl, pentyl, isopentyl, neopentyl, 1-methylbutyl, 2-methylbutyl, 1-ethylpropyl, 1,1-dimethylpropyl, hexyl, isohexyl, 1,1-dimethylbutyl, 2,2-dimethylbutyl, 3,3-dimethylbutyl, 2-ethylbutyl, heptyl, 1-methylhexyl, 2-methylhexyl, 3-methylhexyl, 4-methylhexyl, 5-methylhexyl, 1,1-dimethylpentyl, 2,2-dimethylpentyl, 3,3-dimethylpentyl, 1-ethylpentyl, octyl, nonyl, decyl and the like. The "alkyl having 1 to 10 carbon atoms" for R is preferably alkyl having 5 to 9 carbon atoms, more preferably, alkyl having 7 carbon atoms, more preferably, a heptyl group.

The reduction reaction in Step 1 can be performed in an appropriate inert solvent. Examples of the inert solvent here include ethers (e.g., tetrahydrofuran, diethyl ether), hydrocarbons (e.g., toluene, hexane), halogenated hydrocarbons (e.g., dichloromethane, 1,2-dichloroethane) and the like, and two or more kinds of these may be used in a mixture at an appropriate ratio. The inert solvent is preferably ethers, hydrocarbons or a mixed solvent thereof, more preferably, tetrahydrofuran, toluene or a mixed solvent thereof.

As compound (I), for example, one prepared by the method described in WO 2007/069712 may be used, or a commercially available one may be directly used. While the concentration of compound (I) is not particularly limited, it is, for example, 1 mmol to 100 mmol, preferably 2 mmol to 50 mmol, more preferably 5 mmol to 30 mmol, relative to 100 mL of an inert solvent.

As diisobutylaluminum hydride, a commercially available one may be used, or one obtained by previously dissolving in the above-mentioned inert solvent may be used. While the amount of diisobutylaluminum hydride to be used is not particularly limited, it is, for example, 2 mol to 30 mol, preferably 3 mol to 10 mol, more preferably 4 mol to 6 mol, per 1 mol of compound (I).

The reduction reaction in Step 1 may be started by, for example, adding dropwise diisobutylaluminum hydride previously dissolved in the above-mentioned inert solvent to give a solution of compound (I) in the above-mentioned inert solvent.

The reduction reaction of Step 1 may be performed under an inert gas (e.g., nitrogen, argon and the like) atmosphere.

While the reaction temperature of Step 1 is not particularly limited, it is, for example, 0° C. to 120° C., preferably, 20° C. to 90° C., more preferably 40° C. to 70° C.

While the reaction time of Step 1 is not particularly limited, it is, for example, 5 min to 30 hr, preferably 1 hr to 10 hr.

After the reduction reaction in Step 1, discontinuation of reaction, extraction, washing, drying, solvent removal and the like are performed by general methods. Furthermore, as necessary, purification may be performed by silica gel column chromatography, liquid chromatography, recrystallization and the like. In addition, the obtained product may be directly used without a purification treatment for the next step.

The present invention provides a production method of compound (IV) or a pharmaceutically acceptable acid addition salt thereof, the method comprising dialkyl-phosphonate-esterifying a hydroxyl group of compound (II) obtained in Step 1 (hereinafter the resultant product here is referred to as compound (V)), reacting the resultant compound with compound (III), and hydrolyzing and further reducing the obtained compound (hereinafter to be referred to as compound (VI)). The production method is shown by the following Steps 2 to 4.

(Step 2)

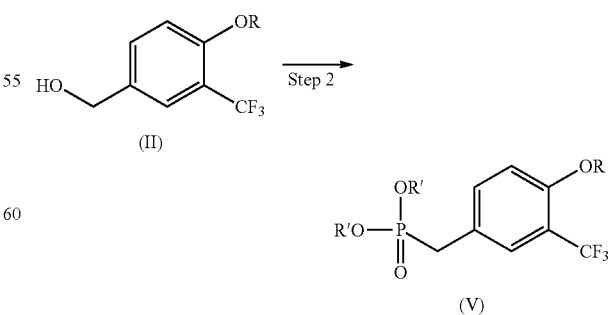

wherein R is as defined above and R' is alkyl having 1 to 3 carbon atoms.

Examples of the "alkyl having 1 to 3 carbon atoms" for R' include methyl, ethyl, propyl and isopropyl. Preferred is methyl or ethyl, more preferred is methyl.

Step 2 can be performed by methods and conditions well known to those of ordinary skill in the art. For example, a hydroxyl group of compound (II) is converted to a leaving group by using a halogenating agent and the like (the resultant product here is referred to as a leaving group form), and Arbuzov reaction using trialkyl phosphite is performed, or dialkyl-phosphonate-esterification using dialkyl phosphite (e.g., dimethyl phosphite etc.) under basic conditions is performed to give compound (V).

The reaction to convert to a leaving group in Step 2 can be performed in an appropriate inert solvent. Examples of the inert solvent here include hydrocarbons (e.g., toluene, hexane), halogenated hydrocarbons (e.g., dichloromethane, chloroform), ethers (e.g., tetrahydrofuran, diethyl ether), ketones (e.g., acetone), amides (e.g., N,N-dimethylformamide), nitriles (e.g., acetonitrile), sulfoxides (e.g., dimethyl sulfoxide) and the like, and two or more kinds of these may be used in a mixture at an appropriate ratio. The inert solvent is preferably hydrocarbons, halogenated hydrocarbons, amides, or a mixed solvent thereof.

While the concentration of compound (II) in the reaction to convert to a leaving group in Step 2 is not particularly limited, it is, for example, 1 mmol to 300 mmol relative of 100 mL of the inert solvent.

Examples of the halogenating agent include chlorinating agents such as concentrated hydrochloric acid, thionyl chloride, oxalyl chloride, phosgene, phosphorus oxychloride, phosphorus pentachloride, phosphorus trichloride; brominating agents such as thionyl bromide, phosphorus tribromide, and the like. The amount of the halogenating agent to be used is, for example, 1 mol to 5 mol, preferably 1 mol to 2 mol, per 1 mol of compound (II). When a halogenating agent is used, a base may be further used. The base usable here include organic bases such as 1,8-diazabicyclo[5.4.0]undec-7-ene (DBU), 1,5-diazabicyclo[4.3.0]non-5-ene (DBN), triethylamine, N,N-diisopropylethylamine, N-methylmorpholine, pyridine, 4-dimethylaminopyridine and the like. The amount of the base to be used is, for example, a catalytic amount.

A reaction to convert to a leaving group (halogenate) can also be similarly performed by Appel reaction by using a combination of triphenylphosphine, carbon tetrachloride and a base instead of the halogenating agent.

While the reaction temperature of the reaction to convert to a leaving group in Step 2 is not particularly limited, it is, for example, −40° C. to 150° C., preferably, −30° C. to 50° C. While the reaction time of the reaction to convert to a leaving group is not particularly limited, it is, for example, 5 min to 30 hr, preferably, 10 min to 6 hr.

After the reaction to convert to a leaving group in Step 2, discontinuation of reaction, extraction, washing, drying, solvent removal and the like are performed by general methods. Furthermore, as necessary, purification may be performed by silica gel column chromatography, liquid chromatography, recrystallization and the like. In addition, the obtained product may be directly used without a purification treatment for the next step.

The dialkyl-phosphonate-esterification reaction in Step 2 may also be performed in an appropriate inert solvent. Examples of the inert solvent here include hydrocarbons (e.g., toluene, xylene, hexane), ethers (e.g., tetrahydrofuran, diethyl ether), ketones (e.g., acetone), amides (e.g., N,N-dimethylformamide), nitriles (e.g., acetonitrile), sulfoxides (e.g., dimethyl sulfoxide) and the like, and two or more kinds of these may be used in a mixture at an appropriate ratio. When dialkyl phosphite is used, the inert solvent is preferably amides.

While the concentration of the leaving group form in the dialkyl-phosphonate-esterification reaction in Step 2 is not particularly limited, it is, for example, 1 mmol to 200 mmol per 100 mL of the inert solvent.

When dialkyl phosphite is used, the amount thereof to be used is, for example, 1 mol to 50 mmol, preferably 1 mol to 20 mol, per 1 mol of the leaving group form.

Examples of the base when dialkyl phosphite is used include inorganic bases such as sodium hydrogen carbonate, potassium hydrogen carbonate, sodium carbonate, potassium carbonate, cesium carbonate, sodium hydride and the like, and organic bases such as triethylamine, diisopropylethylamine, N-methylmorpholine, pyridine, 4-dimethylaminopyridine and the like. The amount of the base to be used is, for example, 1 mol to 10 mol, preferably 1 mol to 5 mol, per 1 mol of the leaving group form.

When dialkyl phosphite is used, a phase-transfer catalyst may be further used. Examples of the phase-transfer catalyst include quaternary ammonium salts such as tetrabutylammonium bromide, tetrabutylammonium iodide and the like, and the like. The amount of the phase-transfer catalyst to be used is, for example, 1 mol to 5 mol, preferably 1 mol to 3 mol, per 1 mol of the leaving group form.

While the reaction temperature when using dialkyl phosphite is not particularly limited, it is, for example, 0° C. to 100° C. While the reaction time when using dialkyl phosphite is not particularly limited, it is, for example, 5 min to 50 hr.

On the other hand, when trialkyl phosphite is used (in the case of Arbuzov reaction), the inert solvent is preferably hydrocarbons such as xylene.

The amount of the trialkyl phosphite to be used for Arbuzov reaction is, for example, 1 mol to excess amount, per 1 mol of the leaving group form.

While the reaction temperature of the Arbuzov reaction is not particularly limited, it is, for example, 100° C. to 170° C. While the reaction time of the Arbuzov reaction is not particularly limited, it is, for example, 30 min to 12 hr.

After the dialkyl-phosphonate-esterification reaction in Step 2, discontinuation of reaction, extraction, washing, drying, solvent removal and the like are performed by general methods. Furthermore, as necessary, purification may be performed by silica gel column chromatography, liquid chromatography, recrystallization and the like. In addition, the obtained product may be directly used without a purification treatment for the next step.

(Step 3)

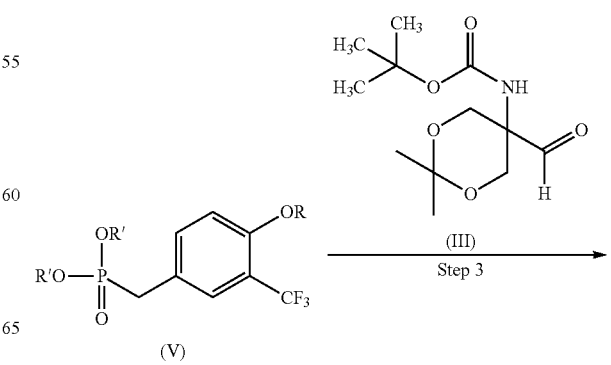

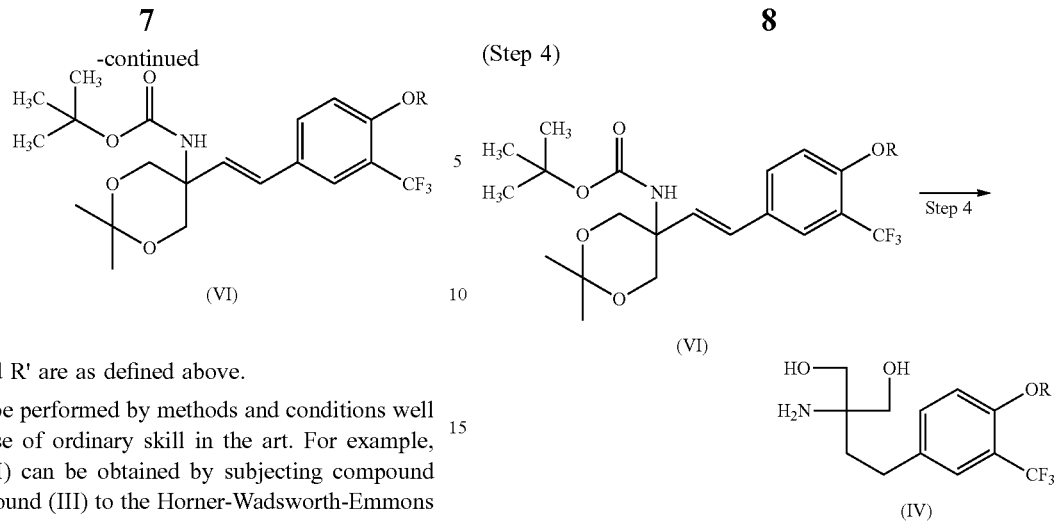

wherein R and R' are as defined above.

Step 3 can be performed by methods and conditions well known to those of ordinary skill in the art. For example, compound (VI) can be obtained by subjecting compound (V) and compound (III) to the Horner-Wadsworth-Emmons reaction in the presence of a base (hereinafter to be referred to as Horner reaction).

The Horner reaction in Step 3 can be performed in an appropriate inert solvent. Examples of the inert solvent include alcohols (e.g., methanol, ethanol), ethers (e.g., tetrahydrofuran, diethyl ether, 1,2-dimethoxyethane), hydrocarbons (e.g., benzene, toluene, hexane), halogenated hydrocarbons (e.g., dichloromethane, chloroform), amides (e.g., N,N-dimethylformamide), sulfoxides (e.g., dimethyl sulfoxide) and the like, and two or more kinds of these may be used in a mixture at an appropriate ratio. The inert solvent is preferably ethers, amides or a mixed solvent thereof.

While the concentration of compound (V) in the Horner reaction in Step 3 is not particularly limited, it is, for example, 1 mmol to 200 mmol per 100 mL of an inert solvent.

As compound (III), for example, one prepared by the method described in WO 2007/069712 may be used, or a commercially available one may be directly used. The amount of compound (III) to be used is, for example, 1 mol to 5 mol, preferably 1 mol to 3 mol, per 1 mol of compound (V).

Examples of the base in the Horner reaction in Step 3 include inorganic bases such as sodium hydride, potassium hydride, sodium methoxide, sodium ethoxide, potassium tert-butoxide, lithium hexamethyldisilazane, sodium hexamethyldisilazane, and potassium hexamethyldisilazane. The amount of the base to be used is, for example, 1 mol to 10 mol per 1 mol of compound (V).

While the reaction temperature of the Horner reaction in Step 3 is not particularly limited, it is, for example, −80° C. to 200° C., preferably −20° C. to refluxing temperature, more preferably −5° C. to 5° C. While the reaction time of the Horner reaction in Step 3 is not particularly limited, it is, for example, 5 min to 50 hr, preferably, 30 min to 12 hr.

After the Horner reaction in Step 3, discontinuation of reaction, extraction, washing, drying, solvent removal and the like are performed by general methods. Furthermore, as necessary, purification may be performed by silica gel column chromatography, liquid chromatography, recrystallization and the like. In addition, the obtained product may be directly used without a purification treatment for the next step.

wherein R is as defined above.

Step 4 can be performed by methods and conditions well known to those of ordinary skill in the art. For example, compound (VI) can be deprotected by subjecting to hydrolysis under acidic conditions (hereinafter the resultant product here is referred to as a hydrolysis resultant product), and olefin is reduced using a hydrogen source and a reduction catalyst to give compound (IV).

The hydrolysis in Step 4 can be performed in an appropriate solvent as necessary. Examples of the solvent here include water, alcohols (e.g., methanol, ethanol, tert-butanol), hydrocarbons (e.g., toluene, hexane), halogenated hydrocarbons (e.g., dichloromethane), ethers (e.g., tetrahydrofuran, diethyl ether), ketones (e.g., acetone), amides (e.g., N,N-dimethylformamide), nitriles (e.g., acetonitrile), sulfoxides (e.g., dimethyl sulfoxide) and the like, and two or more kinds of these may be used in a mixture at an appropriate ratio.

The concentration of compound (VI) in the hydrolysis in Step 4 is not particularly limited as long as it does not exert an adverse influence on the progress of the reaction.

The acid to be used in the hydrolysis in Step 4 is preferably a strong acid. Examples of the strong acid include inorganic strong acids such as hydrochloric acid, sulfuric acid, nitric acid, hydrobromic acid and the like, and organic strong acids such as trifluoroacetic acid, trifluoromethanesulfonic acid and the like. The amount of the strong acid to be used is generally 1 mol to an excess amount per 1 mol of compound (VI).

While the reaction temperature of the hydrolysis reaction in Step 4 is not particularly limited, it is, for example, −20° C. to refluxing temperature, preferably refluxing temperature. While the reaction time of the hydrolysis in Step 4 is not particularly limited, it is, for example, 5 min to 50 hr.

After the hydrolysis in Step 4, discontinuation of reaction, extraction, washing, drying, solvent removal and the like are performed as necessary by general methods. Furthermore, purification may be performed by silica gel column chromatography, liquid chromatography, recrystallization and the like. In addition, the obtained product may be directly used without a purification treatment for the next step.

The reduction reaction in Step 4 can be performed as necessary in an appropriate solvent. Examples of the solvent here include those similar to those used for the hydrolysis. The concentration of the hydrolysis resultant product in the reduction reaction in Step 4 is not particularly limited as long as it does not exert an adverse influence on the progress of the reaction.

Examples of the hydrogen source of the reduction reaction in Step 4 include hydrogen gas, formic acid, sodium formate, ammonium formate, cyclohexene, phosphinic acid salt, hydrazine and the like. When hydrogen gas is used as a hydrogen source, the reaction is performed under a hydrogen pressure of 1 to about 20 atm.

Examples of the reduction catalyst in the reduction reaction in Step 4 include palladium carbon, palladium black, palladium chloride, palladium hydroxide carbon, platinum oxide, platinum black, platinum palladium, platinum carbon, Raney-nickel, Raney-cobalt and the like. The amount of the reduction catalyst to be used is, for example, generally 0.0001 mol to 0.1 mol per 1 mol of a hydrolysis resultant product.

While the reaction temperature of the reduction reaction in Step 4 is not particularly limited, it is, for example, −20° C. to refluxing temperature. While the reaction time of the reduction reaction in Step 4 is not particularly limited, it is, for example, 5 min to 100 hr.

After the reduction reaction in Step 4, discontinuation of reaction, extraction, washing, drying, solvent removal and the like are performed as necessary by general methods. Furthermore, purification may be performed by silica gel column chromatography, liquid chromatography, recrystallization and the like.

In one embodiment, compound (IV) or a pharmaceutically acceptable acid addition salt thereof is preferably 2-amino-2-[2-(4-heptyloxy-3-trifluoromethylphenyl)ethyl]propane-1,3-diol. In another embodiment, compound (IV) or a pharmaceutically acceptable acid addition salt thereof is preferably 2-amino-2-[2-(4-heptyloxy-3-trifluoromethylphenyl)ethyl]propane-1,3-diol hydrochloride.

Examples of the "pharmaceutically acceptable acid addition salt" in the present specification include inorganic acid salts such as hydrochloride, hydrobromide, nitrate, sulfate, phosphate and the like, and organic acid salts such as acetate, tartrate, citrate, fumarate, maleate, toluenesulfonate, methanesulfonate and the like. Preferably, the pharmaceutically acceptable salt is a hydrochloride salt.

Each compound in the production method of the present invention may be a solvate thereof (e.g., hydrate (e.g., monohydrate, dihydrate and the like)) or a non-solvate (e.g., non-hydrate and the like).

Each compound in the production method of the present invention also includes compounds labeled or substituted with an isotope (e.g., $^{2}H$, $^{3}H$, $^{11}C$, $^{14}C$, $^{18}F$, $^{35}S$, $^{125}I$ and the like) and the like.

EXAMPLES

The present invention is further explained in detail by referring to the following Examples. They do not limit the present invention and the present invention may be changed within the range not deviating from the range of the present invention.

Study of Reduction Conditions of
4-heptyloxy-3-trifluoromethylbenzoic Acid

In the following, the reaction conditions of a step of reducing 4-heptyloxy-3-trifluoromethylbenzoic acid (hereinafter to be referred to as compound (Ia)) to 4-heptyloxy-3-trifluoromethylbenzyl alcohol (hereinafter to be referred to as compound (IIa)) were studied.

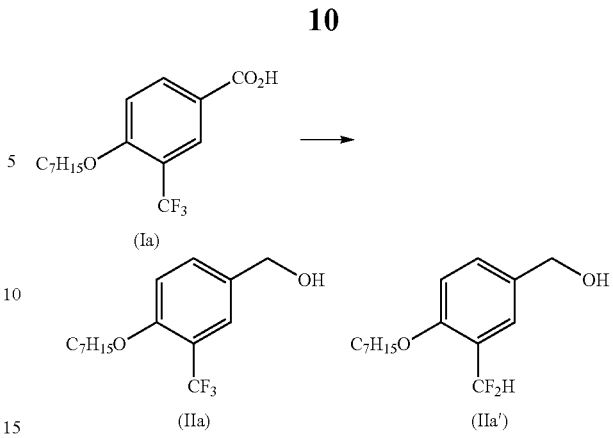

Example 1

Under a nitrogen atmosphere, to a solution of compound (Ia) (30.0 g, 98.6 mmol) in tetrahydrofuran (THF) (240 mL) was added dropwise a solution of 25% diisobutylaluminum hydride (DIBAL) in toluene (332 mL, 493 mmol), and the mixture was heated to 50° C. and stirred for 2 hr. After cooling to room temperature, methanol (15.80 g, 493 mmol) was added dropwise. The obtained solution was added dropwise to 2N hydrochloric acid (296 mL, 592 mmol), and the mixture was stirred at 50° C. to 60° C. for 30 min and analyzed. As a result, the conversion ratio to the object compound (IIa) was 98.4%. On the other hand, a byproduct such as 3-difluoromethyl-4-heptyloxybenzyl alcohol (hereinafter to be referred to as compound (IIa')) was not detected.

Comparative Example 1

To a solution of compound (Ia) (6.50 g, 21.4 mmol) in toluene (45.5 mL) was added dropwise a solution of Red-Al (registered trade mark) (sodium bis(2-methoxyethoxy)aluminum hydride) (16.6 g, 53.4 mmol) in toluene (19.5 mL), and the mixture was stirred at near room temperature for 5 hr and analyzed. As a result, the conversion ratio to the object compound (IIa) was 99.3%. On the other hand, 0.3% of compound (IIa') was produced as a byproduct.

Comparative Example 2

To a mixture of $NaBH_4$ (0.62 g, 16.5 mmol) and THF (6.0 mL) was added dropwise a solution of compound (Ia) (2.0 g, 6.6 mmol) in THF (8.0 mL) at 0° C., and the mixture was stirred at 0° C. for 30 min. To this mixture was added dropwise a solution of trifluoroacetic anhydride (TFA) (1.88 g, 16.5 mmol) in THF (4.0 mL) and the mixture was stirred at room temperature for 3 hr and analyzed. As a result, the conversion ratio to the object compound (IIa) was 12.4%. On the other hand, a byproduct such as compound (IIa') was not detected.

Comparative Example 3

To a solution of compound (Ia) (2.0 g, 6.6 mmol) in THF (14.0 mL) was added dropwise a solution of $BH_3.N,N$-diethylaniline complex (2.26 g, 13.9 mmol) in THF (19.5 mL), and the mixture was stirred at near room temperature for 5 hr and analyzed. As a result, the conversion ratio to the object compound (IIa) was 79.3%. On the other hand, 1.5% of compound (IIa') was produced as a byproduct.

The above results are shown in the following Table 1.

TABLE 1

| | reducing agent (amount used (molar equivalents)) | solvent | temperature (° C.) | time (h) | conversion ratio (%) | by-product (%) |
|---|---|---|---|---|---|---|
| Ex. 1 | DIBAL (5.0) | toluene/THF | 50 | 2 | 98.4 | not detected |
| Comp. Ex. 1 | Red-Al (2.5) | toluene | 20 | 5 | 99.3 | 0.3 |
| Comp. Ex. 2 | NaBH4 (2.5), TFA (2.5) | THF | 30 | 3 | 12.4 | not detected |
| Comp. Ex. 3 | BH3-diethylaniline complex (2.1) | THF | 30 | 5 | 79.3 | 1.5 |

Conversion ratio (%) and byproduct (%) were determined by HPLC analysis.

(HPLC Analysis Conditions)

column: YMC-Pack Pro C18, AS12S05-1506WT (YMC)

column temperature: 40° C.

mobile phase: A 50 mM NaClO$_4$ buffer (pH 2.5), B acetonitrile

Linear concentration gradient from initial concentration of A/B=40/60 to A/B=10/90 40 min later was used.

mobile phase flow rate: 1.0 ml/min analysis time: 40 min

Under the analysis conditions, the retention time of compound (Ia), compound (IIa) and compound (IIa') was about 20.8 min, about 20.2 min and about 17.3 min, respectively.

(Conversion Ratio (%))

$$\frac{\text{(peak area \% of compound (}IIa\text{))}}{\text{(peak area \% of compound (}Ia\text{)) + (peak area \% of compound (}IIa\text{))}} \times 100$$

(Byproduct (%))

peak area % of compound (IIa') relative to total peak (=100%)

Under the reaction conditions of Comparative Examples 1 and 3, byproducts such as compound (IIa') were detected. When compound (IIa') is produced as a byproduct, the reaction conditions are not suitable for the production of a drug substance for a pharmaceutical product requested to have high quality since a series of analogs derived from this compound (IIa') are difficult to remove in the subsequent steps. Under the reaction conditions of Comparative Example 2, a byproduct such as compound (IIa') is not detected; however, the reaction conditions are not similarly suitable, since the conversion ratio to compound (IIa) is low.

Preparation of 2-amino-2-[2-(4-heptyloxy-3-trifluoromethylphenyl)ethyl]propane-1,3-diol Hydrochloride In the following, 2-amino-2-[2-(4-heptyloxy-3-trifluoromethylphenyl)ethyl]propane-1,3-diol hydrochloride was prepared from compound (IIa) based on the route shown in the following scheme.

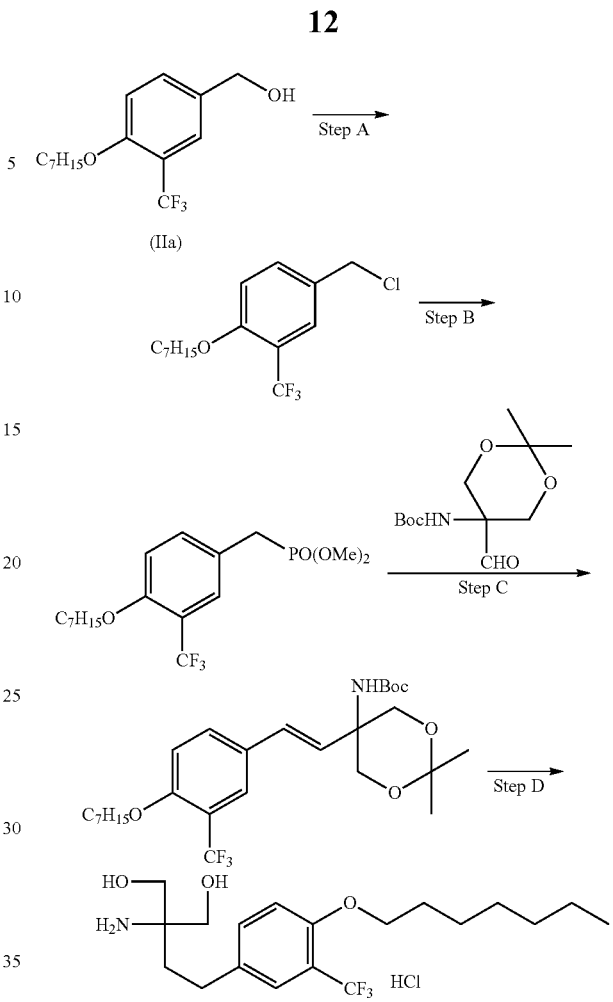

Example 2

Synthesis of 4-heptyloxy-3-trifluoromethylbenzyl Chloride (Step A)

To a solution of compound (IIa) (26.8 g) in methylene chloride (107 mL) was added several drops of N,N-dimethylformamide, and thionyl chloride (8.09 mL) was added dropwise at 0° C. The mixture was stirred at the same temperature for 2 hr, and water (50 mL) was added to the reaction mixture. The organic layer was extracted by partitioning, washed with water (50 mL) and saturated aqueous sodium hydrogen carbonate (70 mL), and dried over anhydrous magnesium sulfate, and the solvent was evaporated under reduced pressure to give 4-heptyloxy-3-trifluoromethylbenzyl chloride (28.3 g) as white crystals.

1H-NMR (CDCl3) δ (ppm): 0.89 (3H, t, J=6.5 Hz), 1.26-1.54 (8H, m), 1.77-1.86 (2H, m), 4.04 (2H, t, J=6.4 Hz), 4.56 (2H, s), 6.96 (1H, d, J=8.6 Hz), 7.49 (1H, dd, J=2.0 Hz, 8.5 Hz), 7.58 (1H, d, J=1.9 Hz)

Example 3

Synthesis of Dimethyl (4-heptyloxy-3-trifluoromethylbenzyl)phosphonate (Step B)

To a solution of 4-heptyloxy-3-trifluoromethylbenzyl chloride (6.00 g, 19.4 mmol) in N,N-dimethylformamide (36 mL) were added dimethyl phosphite (2.57 g, 23.3 mmol), cesium carbonate (7.60 g, 23.3 mmol) and tetrabutylammonium iodide (7.54 g, 20.4 mmol), and the mixture was stirred at 25° C. for 1 day. Toluene (36 mL) and water (18 mL) were added for partitioning, and the obtained organic layer was washed twice with a mixed solution of N,N-dimethylformamide (18 mL) and water (18 mL). After concentration under reduced pressure, column purification using hexane and ethyl acetate was performed to give dimethyl(4-heptyloxy-3-trifluoromethylbenzyl)phosphonate (4.71 g).

MS(ESI) m/z: 383[M+H]

1H-NMR (CDCl3) δ (ppm): 0.89 (3H, t, J=6.9 Hz), 1.20-1.41 (6H, m), 1.43-1.49 (2H, m), 1.72-1.83 (2H, m), 3.09 (1H, s), 3.14 (1H, s), 3.68 (3H, s), 3.70 (3H, s), 4.02 (2H, t, J=6.4 Hz), 6.94 (1H, d, J=8.4 Hz), 7.41-7.44 (2H, m)

Example 4

Synthesis of (E)-{2,2-dimethyl-5-[2-(4-heptyloxy-3-trifluoromethylphenyl)vinyl]-1,3-dioxan-5-yl}carbamic Acid Tert-Butyl Ester (Step C)

A mixed solution of a solution of dimethyl (4-heptyloxy-3-trifluoromethylbenzyl)phosphonate (1.18 g, 3.09 mmol) in N,N-dimethylformamide (1.25 mL) and a solution of (2,2-dimethyl-5-formyl-1,3-dioxan-5-yl)carbamic acid tert-butyl ester (961 mg, 3.71 mmol) in tetrahydrofuran (4 mL) was added dropwise to a solution of potassium tert-butoxide (1.28 g, 11.4 mmol) in tetrahydrofuran (7 mL), and the mixture was stirred at 0° C. for 6 hr. Heptane (7 mL) and water (3 mL) were added for partitioning, and the obtained organic layer was washed twice with water (3 mL) and concentrated. Heptane was added and the mixture was cooled in an ice bath, and the precipitated crystals were collected by filtration, and dried under reduced pressure to give (E)-{2,2-dimethyl-5-[2-(4-heptyloxy-3-trifluoromethylphenyl)vinyl]-1,3-dioxan-5-yl}carbamic acid tert-butyl ester (0.99 g).

MS(ESI) m/z: 516[M+H]

1H-NMR (CDCl3) δ (ppm): 0.89 (3H, t, J=6.9 Hz), 1.29-1.38 (6H, m), 1.44-1.59 (17H, m), 1.77-1.83 (2H, m), 3.83-3.93 (2H, m), 3.93-4.08 (4H, m), 5.21 (1H, brs), 6.10 (1H, brd, J=16.5 Hz), 6.48 (1H, d, J=16.5 Hz), 6.91 (1H, d, J=8.5 Hz), 7.44 (1H, dd, J=8.6, 2.1 Hz), 7.55 (1H, d, J=2.0 Hz)

Example 5

Synthesis of 2-amino-2-[2-(4-heptyloxy-3-trifluoromethylphenyl)ethyl]propane-1,3-diol Hydrochloride (Step D)

A solution of (E)-{2,2-dimethyl-5-[2-(4-heptyloxy-3-trifluoromethylphenyl)vinyl]-1,3-dioxan-5-yl}carbamic acid tert-butyl ester (6.50 g, 12.6 mmol) in methanol (65 mL) was heated to 50° C., a solution of concentrated hydrochloric acid (2.55 g) in methanol (5.3 mL) was added dropwise and the mixture was stirred at 60° C. for 6 hr. After cooling to near room temperature, 5% palladium carbon (0.33 g) was added, and the mixture was stirred under a hydrogen gas atmosphere for 3 hr, filtered, and the residue was washed with methanol (39 mL). The filtrate was concentrated and stirred at 5° C. for 1 hr. Water (32.5 mL) was added and the mixture was stirred at 5° C. for 1 hr. The precipitated crystals were collected by filtration, washed with water (13 mL), and dried under reduced pressure to give 2-amino-2-[2-(4-heptyloxy-3-trifluoromethylphenyl)ethyl]propane-1,3-diol hydrochloride (4.83 g).

MS(ESI) m/z: 378[M+H]

INDUSTRIAL APPLICABILITY

According to the production method of the present invention, 4-alkoxy-3-trifluoromethylbenzyl alcohol can be produced at a high conversion ratio while strictly suppressing the production of a byproduct. Therefore, the production method of the present invention is suitable for the production of a drug substance for a pharmaceutical product requested to have high quality.

This application is based on a patent application No. 2016-149905 filed in Japan on Jul. 29, 2016, the contents of which are incorporated by reference in full herein.

The invention claimed is:

1. A production method for making a compound of formula (II), the method comprising reducing a compound of formula (I) by using diisobutylaluminum hydride:

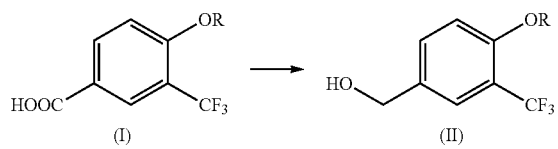

wherein R is alkyl having 1 to 10 carbon atoms, wherein the byproduct of formula (IIa'):

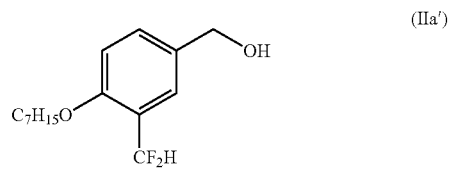

is not detected by HPLC using a C18 column and a mobile phase of 50 mM $NaClO_4$ buffer (pH 2.5) and acetonitrile.

2. A production method for making a compound of formula (IV) or a pharmaceutically acceptable acid addition salt thereof, the method comprising:

reducing a compound of formula (I) by using diisobutylaluminum hydride to provide a compound of formula (II):

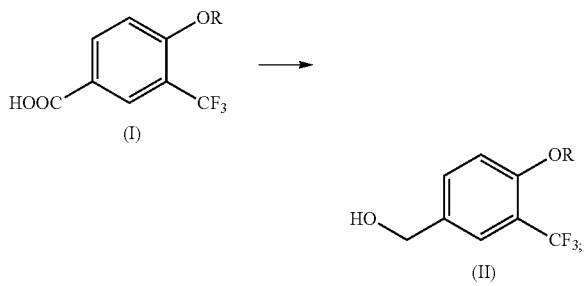

converting the compound of formula (II) to a compound of formula (V):

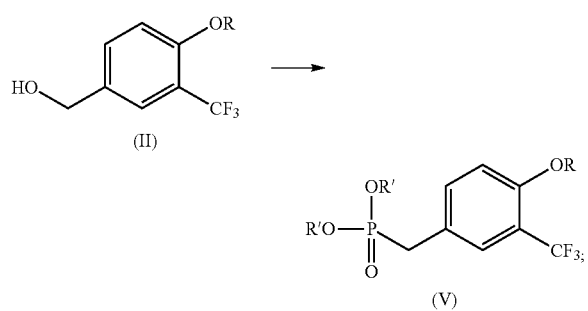

reacting the compound of formula (V) with a compound of formula (III):

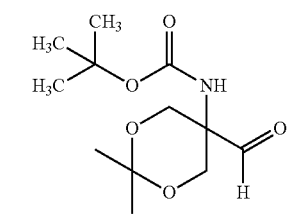

to produce a compound of formula (VI):

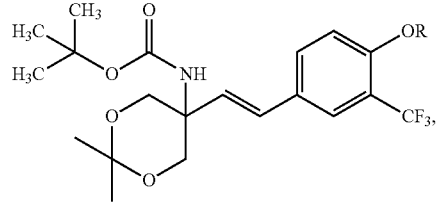

and hydrolyzing and reducing the compound of formula (VI) to produce a compound of formula (IV):

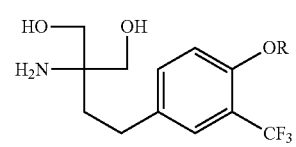

wherein R is alkyl having 1 to 10 carbon atoms, and R' is alkyl having 1 to 3 carbon atoms, wherein the byproduct of formula (IIa'):

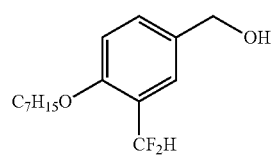

is not detected by HPLC using a C18 column and a mobile phase of 50 mM NaClO$_4$ buffer (pH 2.5) and acetonitrile.

3. The production method according to claim 1, wherein R is a heptyl group.

4. The production method according to claim 2, wherein R is a heptyl group, and the compound represented by the formula (IV) or a pharmaceutically acceptable acid addition salt thereof is 2-amino-2-[2-(4-heptyloxy-3-trifluoromethylphenyl)ethyl]propane-1,3-diol.

5. The production method according to claim 2, wherein R is a heptyl group, and the compound represented by the formula (IV) or a pharmaceutically acceptable acid addition salt thereof is 2-amino-2-[2-(4-heptyloxy-3-trifluoromethylphenyl)ethyl]propane-1,3-diol hydrochloride.

6. The production method according to claim 2, wherein R is a heptyl group.

7. A production method for making a compound of formula (IV) or a pharmaceutically acceptable acid addition salt thereof, the method comprising:

reducing a compound of formula (I) by using diisobutylaluminum hydride to provide a compound of formula (II):

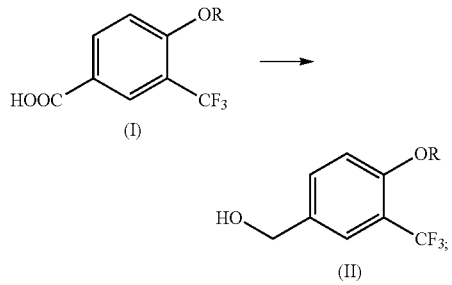

and converting the compound of formula (II) to a compound of formula (IV):

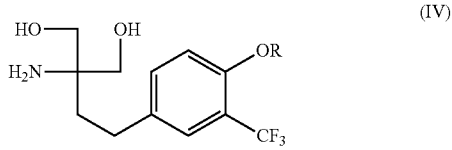

wherein R is alkyl having 1 to 10 carbon atoms, wherein the byproduct of formula (IIa'):

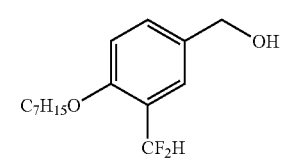

is not detected by HPLC using a C18 column and a mobile phase of 50 mM NaClO$_4$ buffer (pH 2.5) and acetonitrile.

8. The production method according to claim 7, wherein R is a heptyl group.

9. The production method according to claim 7, wherein R is a heptyl group, and the compound represented by the formula (IV) or a pharmaceutically acceptable acid addition salt thereof is 2-amino-2-[2-(4-heptyloxy-3-trifluoromethylphenyl)ethyl]propane-1,3-diol.

10. The production method according to claim 7, wherein R is a heptyl group, and the compound represented by the formula (IV) or a pharmaceutically acceptable acid addition salt thereof is 2-amino-2-[2-(4-heptyloxy-3-trifluoromethylphenyl)ethyl]propane-1,3-diol hydrochloride.

11. The production method according to claim 2, wherein the compound of formula (II) is provided at a high conversion ratio.

12. The production method according to claim 11, wherein the compound of formula (II) is provided at a conversion ratio of greater than 98%.

13. The production method according to claim 7, wherein the compound of formula (II) is provided at a high conversion ratio.

14. The production method according to claim 13, wherein the compound of formula (II) is provided at a conversion ratio of greater than 98%.

15. The production method according to claim 1, further comprising HPLC conditions having (i) a column temperature of 40° C., (ii) a linear concentration gradient of NaClO$_4$ buffer/acetonitrile from an initial concentration of 40/60 to a final concentration of 10/90 for the mobile phase, (iii) a mobile phase flow rate of 1.0 mL/min, and (iv) an analysis time of 40 minutes.

16. The production method according to claim 2, further comprising HPLC conditions having (i) a column temperature of 40° C., (ii) a linear concentration gradient of NaClO$_4$ buffer/acetonitrile from an initial concentration of 40/60 to a final concentration of 10/90 for the mobile phase, (iii) a mobile phase flow rate of 1.0 mL/min, and (iv) an analysis time of 40 minutes.

17. The production method according to claim 7, further comprising HPLC conditions having (i) a column temperature of 40° C., (ii) a linear concentration gradient of NaClO$_4$ buffer/acetonitrile from an initial concentration of 40/60 to a final concentration of 10/90 for the mobile phase, (iii) a mobile phase flow rate of 1.0 mL/min, and (iv) an analysis time of 40 minutes.

* * * * *